United States Patent [19]
Townsend

[11] Patent Number: 5,498,189
[45] Date of Patent: Mar. 12, 1996

[54] ANIMATED FINGER PUPPET

[75] Inventor: Charles P. Townsend, Frinton-on-Sea, United Kingdom

[73] Assignee: Townsend Croquet Limited, Essex, United Kingdom

[21] Appl. No.: 262,299

[22] Filed: Jun. 20, 1994

[30] Foreign Application Priority Data

Jun. 22, 1993 [GB] United Kingdom ............... 9312805

[51] Int. Cl.⁶ ........................................... A63H 3/16
[52] U.S. Cl. .................. 446/100; 446/327; 446/391; 446/394
[58] Field of Search ................. 446/26, 97, 99, 446/100, 321, 327, 328, 391, 394; D21/149, 152, 153, 154; 273/276; 434/86, 270, 271, 256

[56] References Cited

U.S. PATENT DOCUMENTS

| | | | |
|---|---|---|---|
| 129,086 | 7/1872 | Benda | 446/391 |
| 2,253,635 | 8/1941 | Mann | 446/394 |
| 2,302,349 | 11/1942 | Renshaw | 446/327 |
| 3,210,884 | 10/1965 | Sharff et al. | 446/100 |
| 3,765,123 | 10/1973 | Terzian | 446/394 |
| 4,010,570 | 3/1977 | Kohler | 446/327 |
| 4,043,056 | 8/1977 | Savage | 273/157 R |
| 4,050,698 | 9/1977 | Brown | 273/157 R |
| 4,209,919 | 7/1980 | Kirikae et al. | 434/270 |
| 4,504,240 | 3/1985 | Thomas | 446/327 |
| 4,798,556 | 1/1989 | Vicars et al. | 446/391 |
| 4,808,139 | 2/1989 | Price | 446/327 |
| 4,874,345 | 10/1989 | Dirks | 446/394 |
| 5,090,910 | 2/1992 | Narlo | 446/100 |

FOREIGN PATENT DOCUMENTS

| | | | |
|---|---|---|---|
| 3343988 | 6/1984 | Germany | 446/327 |
| 27919 | of 1904 | United Kingdom | 446/391 |
| 4602 | of 1912 | United Kingdom | 446/99 |
| 358838 | 10/1931 | United Kingdom . | |
| 466147 | 5/1937 | United Kingdom . | |
| 701005 | 12/1953 | United Kingdom | 446/327 |
| 1051087 | 12/1966 | United Kingdom | 446/121 |
| 2013508 | 8/1979 | United Kingdom | 446/99 |
| 2091566 | 1/1982 | United Kingdom . | |
| 2219749 | 12/1989 | United Kingdom | 446/327 |

Primary Examiner—Robert A. Hafer
Assistant Examiner—Jeffrey D. Carlson
Attorney, Agent, or Firm—Lowe, Price, LeBlanc & Becker

[57] ABSTRACT

The invention provides a finger puppet comprising a finger stall (30) formed of a resilient material and having a generally tubular configuration with a base area (31) extending generally parallel to the axis of the finger stall on the outer surface thereof. A plurality of inter-changeable human or animal facial head parts (33 to 37), each comprising a portion adapted to be secured to said base area by mutually engaging spigot and bore arrangements is also provided whereby each of said head parts is additionally spatially located on said base area by abutment with a portion of an adjacent head part. The arrangement allows the finger stall to be articulated to provide animation of the features.

18 Claims, 3 Drawing Sheets

ANIMATED FINGER PUPPET

BACKGROUND OF THE INVENTION

The present invention relates to animated finger puppets with replaceable facial displays.

It is an ongoing problem to provide mind-expanding activities for children of the 10 to 14 age group, which are both attractive to the child concerned and cheap enough to be readily replaced if necessary. Educational games and apparatus have as their purpose the advancement of learning and the application of intelligence in a way which is both constructive and enjoyable.

Various attempts have been made to provide human heads with inter-changeable body parts. For example GB-A-466147 describes a human head to which various body parts are attachable, for example eye parts, nose parts, mouth parts, ear parts, hair parts and moustache parts etc. In this disclosure these body parts are each provided with a sharp tack which may be forced into a hollow receptive matrix to secure the part thereto. Whereas the body part may be secured in a such a way initially, the human head matrix will rapidly become pierced with so many holes that it will no longer be able to secure the body parts in any desired inter-relationship.

One solution to this problem has been suggested in GB-A-358838 which relates particularly to opticians models. This provides a face matrix of wood or hard rubber provided with apertures to allow plugs carried by relevant body parts to be engaged therein to reliably secure the same. The stated purpose of this arrangement is to ensure that exactly the same model is presented to a succession of students i.e. that any animation is prevented.

This last arrangement has also been utilised in GB-A-2091566 with the exception that body parts are adapted for ejection from the matrix on rapid arcuate movement thereof. Thus the body parts are loosely retained in bores of the matrix and will fall off if the matrix is moved sharply.

U.S. Pat. No. 5,090,910 (Narlo) relates to a mutable 3-dimensional facial display which is constructed with a plurality of intricately moulded components of a rubbery or polymer material. Each has a defined structural edge which mates with adjacent components to provide seven classic face shapes and many hybrid variations. The difficulty with arrangements of this type is the sheer number of accurate mouldings which are required. This ensures that the final result is so expensive that it is only justifiable as a teaching aid. Further there is no animation.

The inventor has observed that small changes in head parts and their interrelationship, and very small changes in the relative movement of body parts on the face results in perceivable changes in indication of mood. He also found that bending and stretching the forefinger for example could assist in animating a finger puppet. The invention therefore seeks to provide an animated finger puppet with inter-changeable parts for instructional and amusement purposes. Further the finger puppets may by used in conjunction with a skirt which coves the hand. With the finger puppet disposed on, for example, the forefinger, the thumb and second finger can readily animate "arms" in conjunction with the head portion.

OBJECTS OF THE INVENTION

Accordingly the invention has as one object the provision of a simple animated human or animal head model with interchangeable head parts which when in situ on a digit can be made to relatively articulate.

SUMMARY OF THE INVENTION

According to the present invention therefore there is provided a finger puppet comprising a finger stall formed of a resilient material and having a generally tubular digit accommodating configuration,
 a base area extending generally parallel to the axis of the finger stall on the outer surface thereof,
 a plurality of inter-changeable human or animal head parts each comprising a base portion adapted to secured to said base area by a mutually engaging spigot and bore arrangement, and wherein at least some of said head parts are additionally spatially located on said base area by abutment either with a portion of an adjacent head part, or with a cooperating socket portion.

The base area may have an arcuate configuration extending equally about a notional centre line in parallel with the axis of the finger stall, each half of said face area so formed being provided with a plurality of spigot accommodating bores, each said bore being adapted to accommodate a cooperating spigot extending from the rear surface of each of said head parts. This allows each or most head parts to be provided with a pair of spaced spigots each adapted for engagement with spaced bores situated on either side of the notional centre line of the base area. In turn this allows head parts to be moulded in a substantial planar fashion if desired and to be bent to the correct shape during assembly. The spigots may be longitudinally split so as to engage the bore more precisely. Further if the head part is provided with an arcuate cross-section, it is possible by pressing the split spigot into the base to adjust the exterior contour of the head parts relative to the base area.

The head parts may be selected from a hair element, an eye element, a nose element, a mouth element, and a chin and/or beard element. It will be appreciated that head parts above may abut adjacent head parts so as to assist in retaining the same in their correct orientation. Obviously vigorous movement will tend to induce a measure of relative articulation between the head parts and to this end the base area of the finger stall may have a colouring compatible with that of the edges of the adjacent head part.

It is preferable that the eye element and nose element each display a pair of respectively spaced apart eyes and nostrils. This allows the relative spacing of the eyes and nostrils to be maintained during animation.

Each head part is thus formed with a display surface remote from the base portion, said display surface being preferably in 3-dimensions.

The finger stall may be provided with a annular groove adjacent the intended lower end thereof to allow a skirt or cloth body to be secured to the finger stall to obscure the hands from view in use. This skirt or cloth body may be provided with a drawstring for fixing the skirt to the finger stall at the annular groove.

Although the finger stall may be provided with separate ear elements as a head part, it is often generally satisfactory merely to provide ear elements as a portion of the finger stall.

Thus five simple moulded elements and a basic finger stall can form the substance of the invention. The five basic mouldings can have applied thereto different indicia layers to indicate eyes, nose, mouth etc. as desired. These surfaces may be generally smooth in which case the face shape as finally presented will be generally of two dimensions. Alternatively the eyes, nose, mouth etc. may be formed of a 3-dimensional shape and the visual detail applied as a transfer or by painting or printing as appropriate.

The spigots may be of a plain cylindrical configuration or may have a rib or groove disposed thereupon to provide an indication of full engagement when the body part is pressed on to the base area. Alternatively, the spigot may comprise a longitudinal split for spring engagement with the cooperating bore.

In the alternative embodiment, the finger stall may be formed with the first portion comprising the base area and a second portion comprising at least a part of the digit accommodating tubular configuration. This allows the finger stall to be readily moulded in two parts. The two parts may be conjoined by a spigot and bore arrangement or may be adhesively conjoined during manufacture.

The head parts selected in this arrangement may consist of eye elements, nose elements and mouth and chin elements. The ear elements may be moulded in situ adjacent to the base area. By means of this arrangement, a reduced number of mouldings are required to still provide a striking likeness. In a preferred form of the invention, the elements not only interfit with the base area by means of the bore and spigot arrangement, but also are specially confined within socket portions in the base area. In this circumstance, the base area usually comprises the cheek area of the puppet. By this means, the lines of conjunction between the elements and the base area, and the base area and the second portion comprising the cranial area of the puppet, conjoin along natural lines of conjunction and thereby reduce the visual discontinuity which may otherwise be occasioned. By inserting the head elements within a socket portion, these are retained with certainty even during vigorous animation.

The cranial portion of a puppet head may be provided with means for releasably securing at least one hair piece thereto. The hair piece may comprise a shell interfittable with the cranial portion, optionally in a socket provided therein, said shell being provided with a plurality of generally arcuate resilient slots for the retention of a thread such as wool for the representation of hair.

Although the invention has been generally described with reference to the human head, animal heads can also be readily produced by the same method. Indeed kits of parts including a finger stall with a base area and human and/or animal features can be provided so that the heads of hybrid or mythical animals and humanoids can be readily formed. For example the mouth parts of a normal human head can be readily provided with overhanging teeth to provide a vampire, and the nose portion can be rendered excessively hairy to denote a werewolf etc. Similarly straight forward animal heads such as pigs, foxes, bears etc. can be also formed on the same base area.

BRIEF DESCRIPTION OF THE DRAWINGS

The invention will now be described, by way of illustration only, with reference to the accompanying drawings wherein.

DETAILED DESCRIPTION OF THE DRAWINGS

Figure 1:
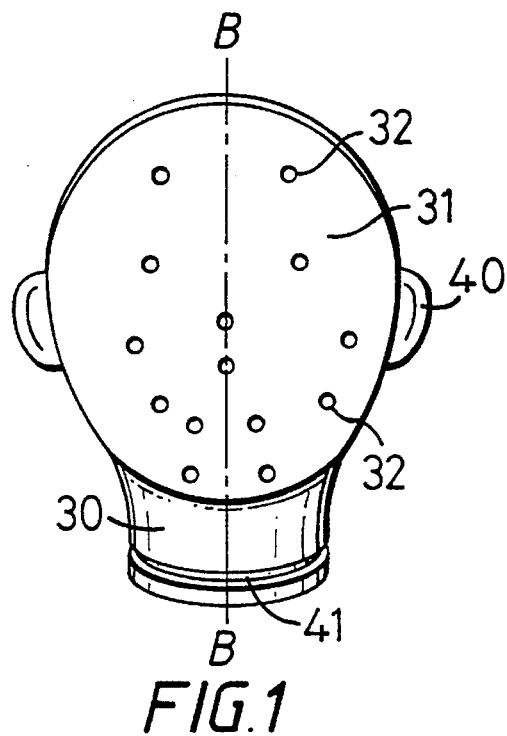
FIG. 1 shows a vertical front elevation of a finger stall in accordance to the present invention showing a base area.

A finger stall (30) is provided with a digit accommodating bore (42) having, for example, a length of 4 to 7 cm and a width such that a child's digit can be slipped thereinto. The finger stall (30) is formed of resilient plastic material or of a natural or synthetic rubber, such that passage of a larger (adult) finger into the digit accommodating bore (42) can be readily accommodated. The basic shape of the finger stall (30) provides a cranial portion (39) extending rearwardly of the digit accommodating bore (42), a base area (31) remote from the cranial area (39) and extending generally in parallel to the axis of the digit accommodating bore (42). Adjacent the entrance to the digit accommodating bore (42) is an annular groove (41) to accommodate a drawstring (not shown) for securing a skirt or cloth body. In the present embodiment ear portions (40) are moulded contemporaneously with the moulding of the finger stall (30), although in other embodiments ear elements (40) may be securable to the base area by the methods below.

The base area (31) is a generally ovoid area in plan and extends generally parallel to and arcuately about the axis of the digit accommodating bore (42) so as to impose a 3-dimensional configuration even when the display faces of head parts, to be elucidated later, are essentially initially planar.

Figure 2:
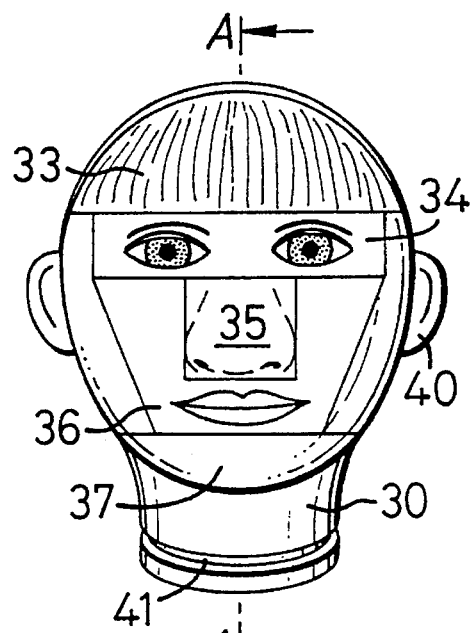
FIG. 2 shows a front vertical elevational view of the finger stall to which facial elements have been applied.

In a kit for utilization with the base area (31) are a plurality of hair elements (33), eye elements (34), nose elements (35), mouth elements (36), and chin and beard elements (37). Each is provided with a contact face bearing a spigot (38) for cooperation with a blind bore (32). Each of the elements (33 to 37) may be moulded either with an arcuate contact portion including the spigot, or a generally planar configuration. The securing of the spigot (38) in each case into the blind bore (32) locates a respective body part and secures it generally as shown in FIG. 2. It will be appreciated that the hair element (33) can be readily replaced by others so that an approximation of a friend or neighbour can be readily provided. Similar remarks apply to the eye element (34) and nose element (35), the mouth and cheek elements (36) and the chin element (37). All of these with the exception of the nose element are provided with spigots and blind bores located in spaced apart relation on either side of the centre line (B) shown in FIG. 1 so as to secure the said element even during vigorous animation. The nose portion may be secured by upper and lower spigots and bores, although spaced apart bores are of equal utility.

In the at rest position the elements (35) to (37) are all located not only by the blind bores but by abutment of the edges of the moulded elements with each other. As will be seen from the vertical cross-section in FIG. 3 the elements have depth and this allows for their retention in a predetermined orientation.

Figure 3:
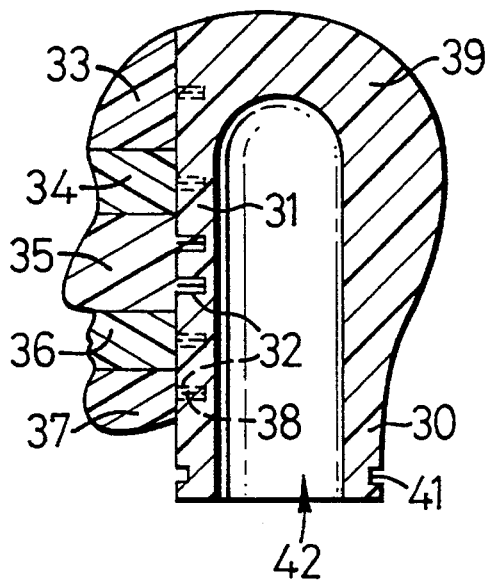
FIG. 3 shows a vertical section along a line AA of FIG. 2.

As shown in FIG. 3 the elements have been formed in three dimensions and plainly this is more satisfactory. However a cheaper version is possible wherein the elements are all provided on a planar sheet with spigots correctly orientated and with body part information printed thereon in two dimensions. Although this is less satisfactory in terms of visual appeal, it makes for a cheaper kit.

By providing a number of inter-changeable elements which spatially interrelate it is possible with careful graphics to change the mood, sex and shape of a human head. Thus it is possible to provide not only animal human heads, but heads of beasts such as vampires, werewolves, etc.

Figure 4:
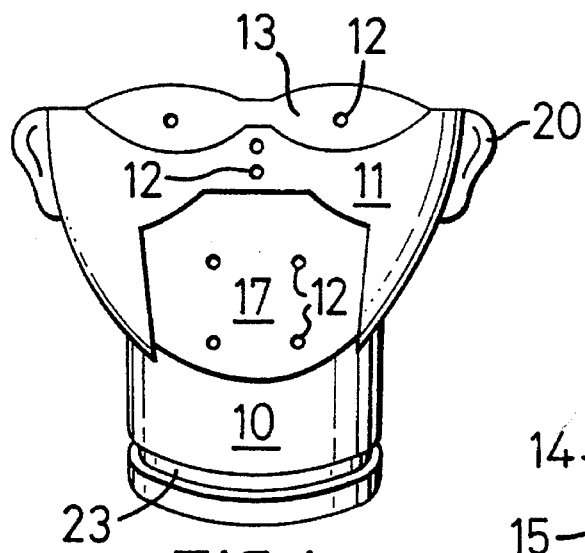
FIG. 4 shows a front vertical elevational view of a finger stall in accordance with a second embodiment of the invention showing a base area.
Figure 5:
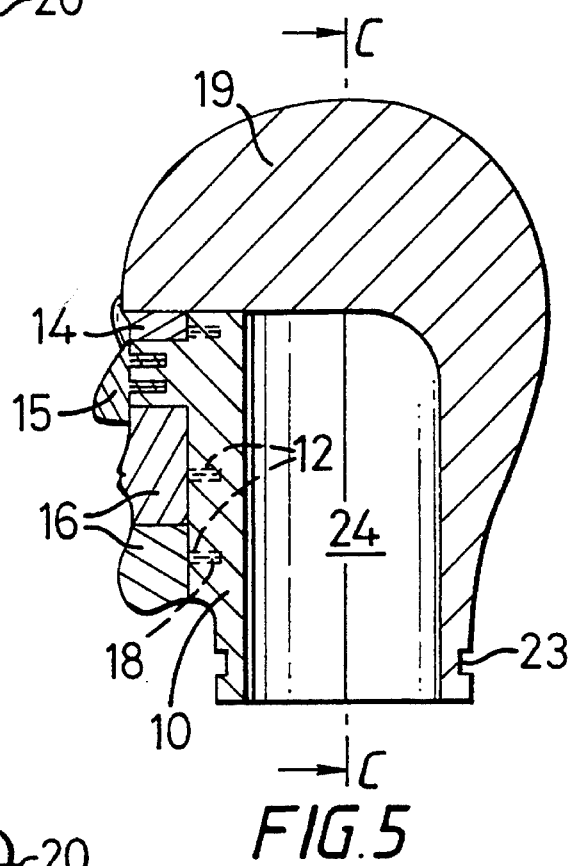
FIG. 5 shows in vertical cross-section an assembly with FIG. 6.
Figure 6:
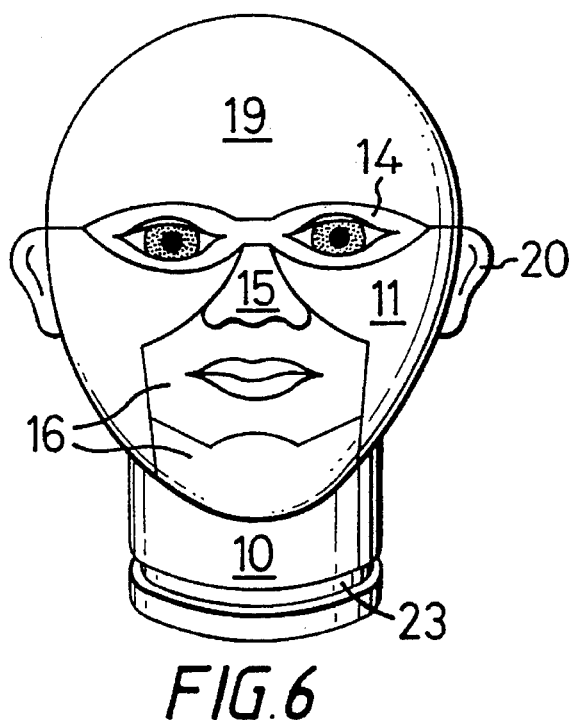
FIG. 6 shows a front elevational view of the finger stall of FIGS. 4 and 5 with facial elements attached.
Figure 7:
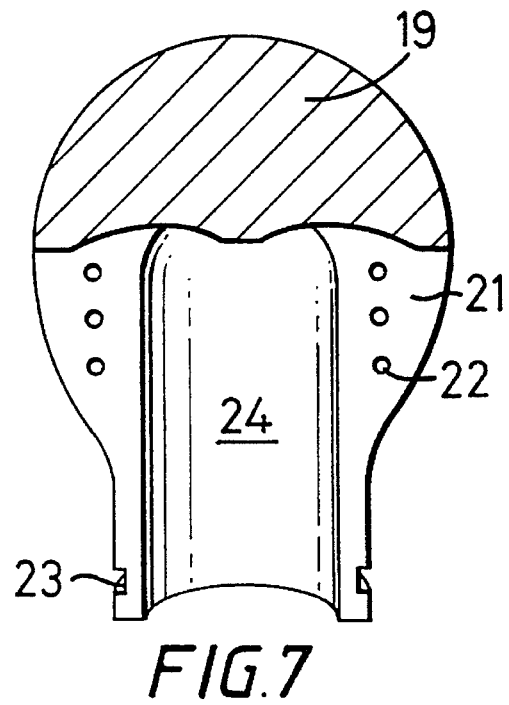
FIG. 7 shows the vertical cross section along a line C—C of FIG. 5.

In a second embodiment shown in FIGS. 4–7, there is provided an alternative form of finger puppet with a finger stall formed of a base portion (10) and an alternative cranial portion (19). The portions (10) and (19) are adapted to be conjoined either by adhesion or other means so as to adopt the configuration as shown in FIG. 5. This may be achieved by providing as is shown in FIG. 7 a plurality of blind bores (22) for cooperating spigots (not shown) so as to bring the surface contact faces (21) to retained abutment. This allows the finger stall (10) to be readily manufactured from two easily moulded halves from an elastomeric material. The conjunction of the contact faces (21) forms inter alia a digit accommodating bore (24) as shown more clearly in FIG. 5.

In a further arrangement of this type, the second cranial portion and the base portion may be conjoined, for example, by a spigot and bore arrangement. There may be a plurality of base areas provided so that when the puppet is put together, different base areas can be selected prior to the addition of the nose, eyes and mouth and chin elements.

As is shown in FIG. 4, the base area is comprised of the lower portion of a human or humanoid face and is moulded with ear portions (20) disposed generally perpendicular to the axis of the bore (24). The lower face moulding (11) thereby formed is provided with eye socket portions (13), mouth and chin socket portions (17), and with a plurality of spaced blind bores (12) for purposes to be elucidated below. The finger stall (10) is also provided adjacent its lower edge with an annular groove (23) to accommodate means from attaching a skirt to the puppet to overlay the hand.

The eye socket portions (13) and the mouth and chin socket portions (17), are constructed and arranged such that when an eye element (14) or mouth and chin elements (16) are engaged therewith, they are constrained structurally by means of the edges of the socket as well as inter-engagement of spigots (18) on the underside of the eye, mouth and chin elements which engage in respective blind bores (12). A nose portion (15) similarly locates on blind bores (12) and may overlay one or more of the eye elements (14) or the mouth and chin elements (16). The eye elements (14) may extend upwardly so as to overlie at least a portion of the cranial moulding (19) which forms part of the finger stall assembly (10).

The lower face moulding (11) is provided with a colouring and a configuration consistent with the eye elements (14) and mouth and chin elements (16) whereby the lines of conjunction are arranged as near as possible to conform to the parameters of the human or humanoid face so that the points of conjunction are not too obvious.

In use, a finger or other digit is inserted in the digit accommodating bore (24) and one of a selection of eye elements is inserted in the socket (13) as such that the spigots on the underside thereof engage with the blind bores (12) in the base area. Similarly, the mouth and chin socket portion (17) is conjoined with one of a plurality of mouth and chin elements (16). Nose element (15) is then selected and disposed as shown in FIG. 6. If the figure is unsatisfactory, one or more of the elements may be replaced until a satisfactory likenesses achieved.

It can be appreciated that this arrangement requires a reduced number of mouldings to provide an animated finger puppet with a satisfactory visual appearance.

Figure 8A:
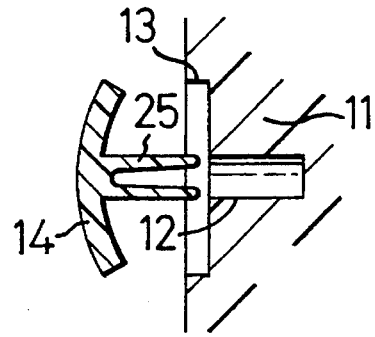
FIG. 8A shows an enlarged transverse section cross section through a spigot and bore assembly prior to assembly.
Figure 8B:
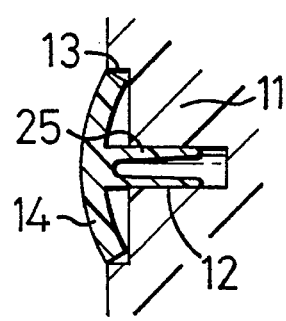
FIG. 8B shows an assembled spigot and bore for assembly in the first position.
Figure 8C:
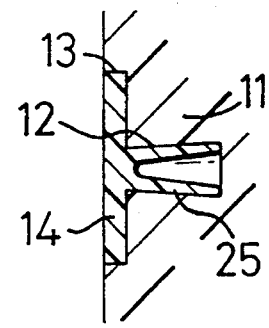
FIG. 8C shows an assembled spigot and bore assembly in a second fully engaged position.

In FIGS. 8A to 8C an eye element (14) is shown by way of example which interfits with an eye socket (13). The principle applies however to other head parts, with or without a cooperating socket.

In the instance shown in FIGS. 8A to 8C the head part (eye part) (14) is provided with a split spigot formed of a resilient material. The blind bore 12 has a slightly convergent cross-section so that as the spigot (25) is pressed home the split ends of the spigot are put under compression.

At the same time, the eye element (14) is moulded with an arcuate configuration and accordingly in a first position as shown in FIG. 8B the eye element has a "pop-eye" configuration which can be progressively flattened to take up the position shown in FIG. 8C by gradually pressing the eye element (14) and hence the spigot (25) into the bore (12). This allows a plurality of eye designs to be applied to a single moulded type whilst also allowing for various visual effects use.

Figure 9:
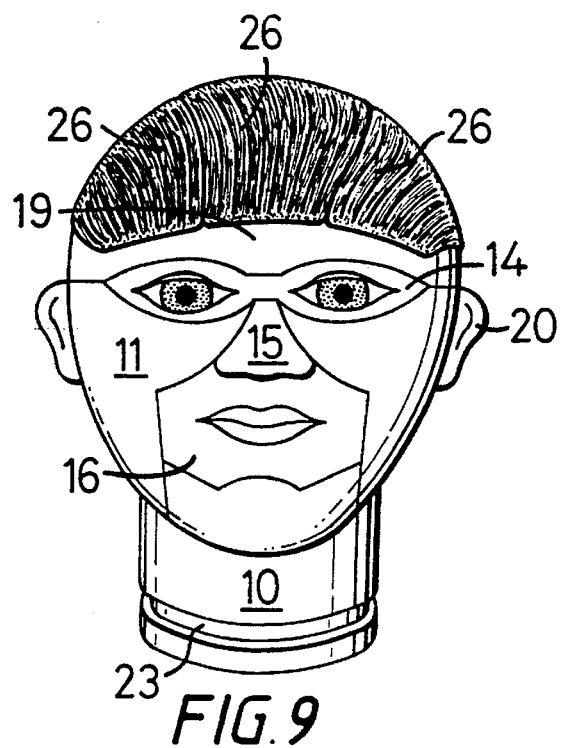
FIG. 9 shows a view similar to that of FIG. 6 but showing assembled hair elements.

FIG. 9 shows a view similar to that described in FIG. 6 but also showing hair attached to the cranial portion (19). To secure the hair pierces (26) a number of Velcro or other adhesive tabs are secured to the cranial portion (19). The kit comprises for example three colours and three lengths of a fur fabric cut to a predetermined shape and or length; for example in the shape of pentangles. The hair pieces (26) can then be secured as shown in FIG. 9. If a balding head is required it is only necessary to remove one or more of hair pieces (26).

Figure 10:
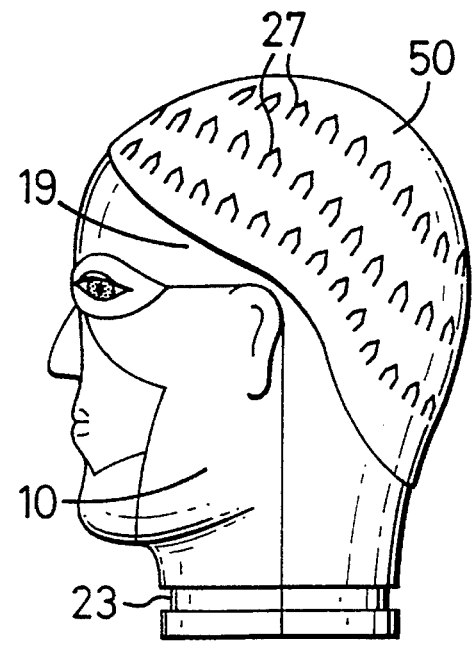
FIG. 10 shows a view similar to that of FIG. 6 but showing an alternative form of hair formation.
Figure 11:
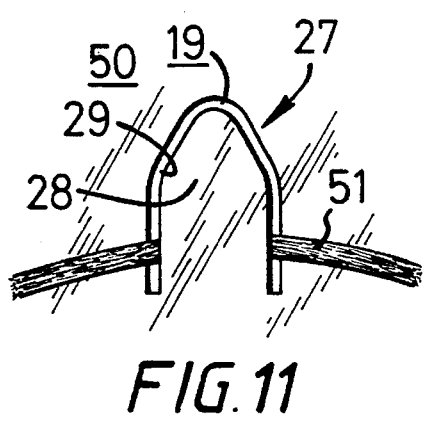
FIG. 11 shows a plan view from above of a slot arrangement for use in FIG. 10.
Figure 12:
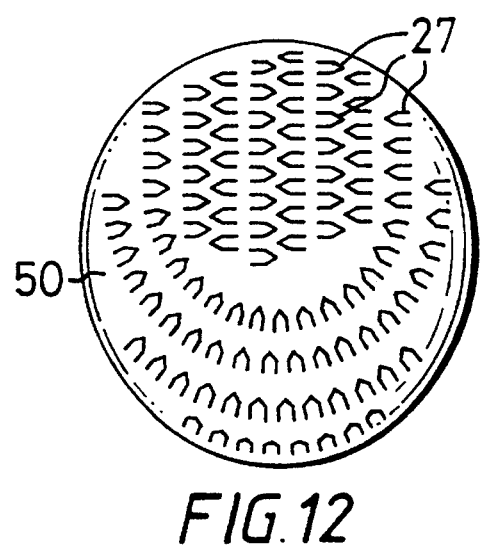
FIG. 12 shows a plan view from above of a shell showing alignment of slots.

In an alternative embodiment as shown in FIGS. 10–12, a thin plastic shell (50) fits over, or into a socket on, the cranial portion (19) of the finger puppet as previously described. The plastic shell (50) is conjoined thereto by any convenient clamping arrangement as by a measure of resilience in the shell itself and/or by means of a spigot and bore arrangement as previously described. The plastic shell may be transparent or may be coloured to an approximation of an intended skin colour.

As shown in FIG. 11, the plastic shell (50) is provided with a plurality of shaped slots (27). These slots (27) which in this instance have a width of about 4 mm have a generally u-shaped configuration with a central resilient tongue portion (28) to define a cut-out area (29) to secure a length of wool (51). The slots are arranged about the shell shown in FIG. 12.

To form the hair, wool or a similar thread material is threaded about the slots so that a portion of the length of each thread is retained by the resilience of the tongue portions (28) against the cranial portion (19). Optionally, serrations (not shown) can be provided on the tongue (28) and/or edges of the slot (29) to retain the wool or other thread in its desired position. In order to complete the "hair piece", wool may be applied as a series of loops between slots (27) and subsequently cut to length to provide the desired hair shape. Various colours and lengths of wool may be selected at will for a desired effect.

If it is desired to make the hair thicker, two or more strands of wool may be secured in one or more slots. Further, because the shell (50) is of a skin colour, no wool may be threaded where bald batches are required.

As shown in FIG. 12, there are three rows of slots facing each other over the intended top of the cranial portion 19. This ensures that "partings" can be readily achieved. Additionally, the shell (50) comprises 4 u-shaped sets of spaced slots (27) to provide a hair portion over the back of the head and neck.

The invention therefore provides an animated puppet secured to a finger stall, and a kit of parts used for the same.

I claim:

1. A finger puppet comprising:
   a finger stall formed of a resilient material and including an axis and a digit accommodating bore adapted to receive a tubular digit therein;
   a base area extending generally parallel to the finger stall axis on the outer surface thereof, the base area including a plurality of bores disposed therein;
   a plurality of interchangeable head parts, each comprising a facial portion and including a spigot protruding from a rear surface thereof, each of said plurality of bores being adapted to accommodate a cooperating spigot extending from the rear surface of a selected head part;
   means for animating the facial portion when articulating the finger stall, said animating means including abutment of at least some of the head parts with a portion of an adjacent head part; and
   a cranial portion disposed on the finger stall adjacent to the base area and including means for releasably securing a hair piece thereto, the hair piece comprising a shell interfittable with the cranial portion, the shell being provided with a plurality of generally arcuate resilient slots, each slot including a resilient tongue portion capable of receiving and retaining at least one thread between the tongue portion and the cranial portion.

2. A finger puppet according to claim 1 wherein the base area has an arcuate configuration extending symmetrically about a central axis thereof and parallel to the finger stall axis.

3. A finger puppet according to claim 2, wherein the plurality of bores are disposed uniformly about the center axis.

4. A finger puppet according to claim 1, wherein the head parts comprise one or more of a hair element, an eye element, a nose element, a mouth element, and a chin/beard element.

5. A finger puppet according to claim 1, wherein each of the plurality of spigots is formed of a resilient material and includes a split shaft.

6. A finger puppet according to claim 1, wherein each head part includes a display surface apposing the rear surface, the display surface being in three dimensions to accentuate facial features.

7. A finger puppet according to claim 1, wherein the finger stall is provided with an annular groove adjacent the lower end thereof to allow a skirt or cloth body to be secured to the finger stall to obscure the hand in use.

8. A finger puppet according to claim 1, wherein the finger stall is formed of a first portion comprising the base area and a second cooperating portion comprising at least part of the digit accommodating bore, the first and second portions being readily and separable from each other.

9. A kit of parts for utilization as a finger puppet, said kit of parts comprising a shaped finger stall including a base area and a cranial portion disposed near the base area, a hair piece, plurality of eye elements, a plurality of nose elements, a plurality of mouth elements, and a plurality of chin/beard elements, wherein the cranial portion includes a means for releasably securing the hair piece thereto, the hair piece comprising a shell interfittable with the cranial portion, the shell being provided with a plurality of generally arcuate resilient slots, each slot including a resilient tongue portion capable of receiving and retaining at least one thread between the tongue portion and the cranial portion.

10. A finger puppet comprising:
    a finger stall formed of a resilient material and including an axis and a digit accommodating bore adapted to receive a tubular digit therein, the finger stall being formed of a first portion comprising the base area and a second cooperating portion comprising at least part of the digit accommodating bore, the first and second portions being readily separable from each other;
    a base area extending generally parallel to the finger stall axis on the outer surface thereof, the base area including a plurality of bores disposed therein;
    a plurality of interchangeable head parts, each comprising a facial portion and including a spigot protruding from a rear surface thereof, each of said plurality of bores being adapted to accommodate a cooperating spigot extending from the rear surface of a selected head part; and
    means for animating the facial portion when articulating the finger stall, said animating means including abutment of at least some of the head parts with a portion of an adjacent head part.

11. A finger puppet according to claim 10, wherein the base area has an arcuate configuration extending symmetrically about a central axis thereof and parallel to the finger stall axis.

12. A finger puppet according to claim 10, wherein the plurality of bores are disposed uniformly about the center axis.

13. A finger puppet according to claim 10, wherein the head parts comprise one or more of a hair element, an eye element, a nose element, a mouth element, and a chin/beard element.

14. A finger puppet according to claim 10, wherein each of the plurality of spigots is formed of a resilient material and includes a split shaft.

15. A finger puppet according to claim 10, wherein each head part includes a display surface apposing the rear surface, the display surface being in three dimensions to accentuate facial features.

16. A finger puppet according to claim 10, wherein the finger stall is provided with an annular groove adjacent the lower end thereof to allow a skirt or cloth body to be secured to the finger stall to obscure the hand in use.

17. A finger puppet according to claim 10, further comprising a plurality of first portions interchangeable with each other.

18. A kit of parts for utilization as a finger puppet, said kit of parts comprising a shaped finger stall including a base area and a cranial portion disposed near the base area, a plurality of hair elements, a hair piece, a plurality of eye elements, a plurality of nose elements, a plurality of mouth elements, and a plurality of chin/beard elements, the stall comprising two inter-fitting finger stall portions, one of said portions comprising the base area, the other of said portions comprising the head area, wherein the finger stall is formed of a first portion comprising the base area and a second cooperating portion comprising at least part of the digit accommodating bore, the first and second portions being readily separable from each other, wherein the cranial portion includes a means for releasably securing the hair piece thereto, the hair piece comprising a shell interfittable with the cranial portion, the shell being provided with a plurality of generally arcuate resilient slots, each slot including a resilient tongue portion capable of receiving and retaining at least one thread between the tongue portion and the cranial portion.

* * * * *